United States Patent
O'Heeron et al.

(10) Patent No.: US 6,835,201 B2
(45) Date of Patent: Dec. 28, 2004

(54) TROCAR

(75) Inventors: Peter T. O'Heeron, Houston, TX (US); Terry L. Bohannon, Houston, TX (US); Patrick T. Davis, Houston, TX (US)

(73) Assignee: NeoSurg Technologies, Inc., Houston, TX (US)

( * ) Notice: Subject to any disclaimer, the term of this patent is extended or adjusted under 35 U.S.C. 154(b) by 428 days.

(21) Appl. No.: 09/809,648

(22) Filed: Mar. 15, 2001

(65) Prior Publication Data

US 2002/0133188 A1 Sep. 19, 2002

(51) Int. Cl.$^7$ ................................. A61B 17/32
(52) U.S. Cl. ........................... 606/184; 606/167
(58) Field of Search ....................... 606/167–168, 606/169–170, 171–175, 176–180, 181–186, 190; 604/164.01–164.03, 164.06, 170.01, 170.02, 264; 600/562–567

(56) References Cited

U.S. PATENT DOCUMENTS 5,545,150 A * 8/1996 Danks et al.
5,569,292 A * 10/1996 Scwemberger et al.
5,571,133 A * 11/1996 Yoon
5,676,683 A * 10/1997 Yoon
5,810,863 A * 9/1998 Wolf et al.
5,817,061 A * 10/1998 Goodwin et al.
5,941,852 A * 8/1999 Dunlap et al.
6,063,099 A * 5/2000 Danks et al.
6,106,539 A * 8/2000 Fortier

* cited by examiner

Primary Examiner—Anhtuan T. Nguyen
Assistant Examiner—Jessica R. Baxter
(74) Attorney, Agent, or Firm—Clarence E. Eriksen

(57) ABSTRACT

A trocar is disclosed which comprises a body assembly and a cannula assembly attached to the body assembly to define a bore therethrough. The disclosed trocar also includes an obturator assembly for sliding engagement in the bore. The obturator assembly comprises a shaft having a longitudinal axis and having a distal end for insertion into a patient. The distal end of the obturator includes a tip which is non-conical and which has upper and lower faces that taper away from the shaft to form a V-shaped distal end of the tip. Wing elements provided between the upper and lower faces proximate the distal end of the tip, and the wing elements are spaced apart approximately 180 degrees from one another. The tip of the obturator may also include dorsal elements on the upper and lower faces.

2 Claims, 2 Drawing Sheets

TROCAR

BACKGROUND OF THE INVENTION

1. Field of the Invention

The present invention relates to surgical instruments known as trocars which are used in endoscopic surgery to pierce or puncture an anatomical cavity to provide communication with the cavity during a surgical procedure. More particularly, the present invention relates to an improved tip for the obturator of the trocar.

2. Description of the Prior Art

Endoscopic surgery constitutes a significant method of performing surgeries and has become the surgical procedure of choice, because of its patient care advantages over "open surgery." One form of endoscopic surgery is laparoscopic surgery, and a significant advantage of laparoscopic surgery over open surgery is the decreased post-operative recovery time. In most instances, a patient is able to leave the hospital within hours after laparoscopic surgery has been performed, whereas multi-day hospitalization is necessary to recover from open surgical procedures. Further, laparoscopic surgery provides decreased incidents of post-operative abdominal adhesions and decreased post-operative pain. Cosmetic results are also enhanced with laparoscopic surgery.

Conventionally, a laparoscopic surgical procedure begins with the insufflation of the abdominal cavity with carbon dioxide. The introduction of this gas into the abdominal cavity lifts the abdominal wall away from the internal viscera. The abdominal wall is then penetrated with a device known as a trocar, which includes a body assembly, a cannula assembly attached to the body assembly to form a bore through the body assembly, and a pointed element called an obturator. The obturator slides in the bore of the trocar and has a piercing tip at its end. After insertion of the trocar through the abdominal wall of the patient, the obturator is removed by the surgeon while leaving the cannula or tube protruding through the body wall. Laparoscopic instruments can then be inserted through the cannula to view internal organs and to perform surgical procedures.

The tip of the obturator of a trocar has traditionally employed a sharp cutting blade to assist the surgeon in penetrating the abdominal wall. However, certain trocars, for example, as disclosed in U.S. Pat. No. 5,817,601 to Goodwin, have employed a pair of blunt-edged blades or tissue separators which are located on the tip of the trocar to facilitate the penetration or dissection of tissue.

The trocar assembly disclosed in U.S. Pat. No. 5,817,061 to Goodwin and U.S. Pat. No. 5,591,192 to Privitera are manufactured and sold by Ethicon Endo-Surgery, Inc. Trocars as described in the '061 and '192 patents have at the time of filing this application been recalled by Ethicon since the tip of the obturator has been prone to failure. In particular, the tip of the trocars disclosed in the '061 and '192 patents have experienced incidents of snapping off during the insertion of the trocar. It is believed that this failure may be attributable to the blunt shape of the tip and the forces to which the tip is subjected upon insertion.

SUMMARY OF THE INVENTION

In accordance with the present invention, a trocar is provided which comprises a body assembly and a cannula assembly which is attached to the body assembly to define a bore therethrough. A trocar in accordance with the present invention also includes an obturator assembly for sliding engagement in the bore. The obturator assembly comprises a shaft having a longitudinal axis and having a distal end for insertion into the body of a patient. The distal end of the obturator includes a tip which is non-conical and which has upper and lower faces which taper away from the shaft to form a V-shaped distal end of the tip. Wing elements are provided between the upper and lower faces proximate the distal end of the obturator. The wing elements are spaced approximately 180 degrees from one another, and the wing elements may be blunt or they may have sharp cutting edges.

A trocar in accordance with the present invention may further comprise dorsal elements on the upper and lower faces. These dorsal elements also facilitate the insertion of the trocar.

By using the foregoing design for the tip of the obturator, the penetration forces associated with insertion of the trocar into a patient are directed away from the tip of the obturator. Also, less insertion force being required to insert a trocar of the present invention as compared to the force required to insert existing blunt tip trocars. The wing and dorsal elements also widen and dilate the wound track to ease entry of the trocar into the wound area.

In a preferred embodiment of the present invention, the obturator tip is releaseably engaged with the shaft of obturator, so that the same trocar may be used with either blunt wing elements or wing elements having sharp cutting edges.

DESCRIPTION OF SPECIFIC EMBODIMENT

Figure 1:
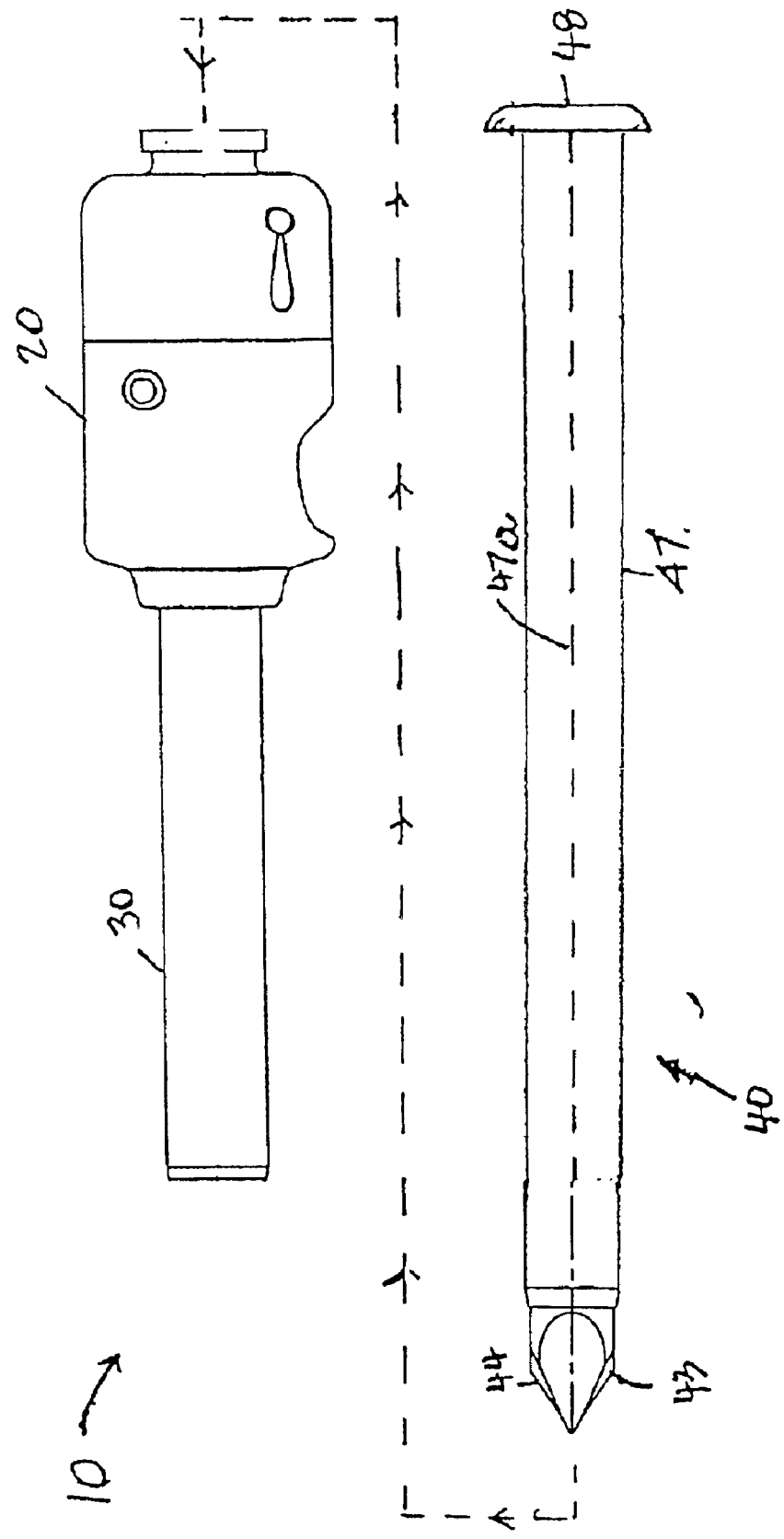
FIG. 1 is an exploded perspective view of an embodiment of a trocar in accordance with the present invention.

With reference to FIG. 1, trocar 10 in accordance with the present invention comprises a body assembly 20 to which is attached a cannula assembly 30. The cannula assembly 30 is a hollow tube, and when attached to the body assembly 20, a bore is defined through the trocar 10.

A trocar in accordance with the present invention also includes an obturator assembly 40 having a shaft 47 having a central longitudinal axis 47a. The proximal end of shaft 47 has an arcuate-shaped cap 48, and the distal end of shaft 47 has a tip for insertion into the patient. The obturator assembly 40 slides in the bore that is defined by the combination of body assembly 20 and cannula assembly 30. While the obturator shaft is preferably formed from a stainless steel material, those skilled in the art will appreciate that the obturator shaft may be formed from a variety of suitable materials.

Figure 2:
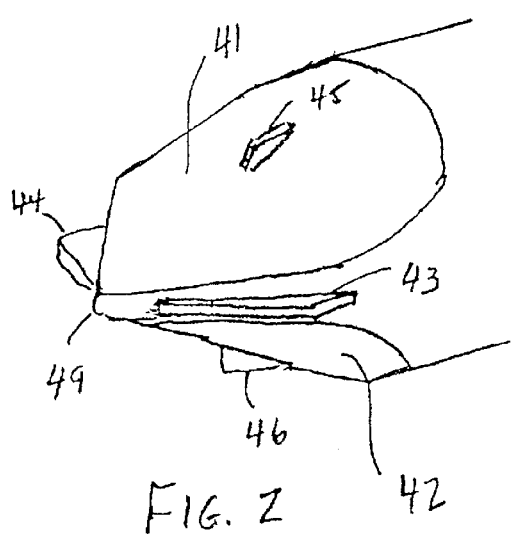
FIG. 2 is a perspective view of a tip for a trocar in accordance with the present invention.
Figure 3:
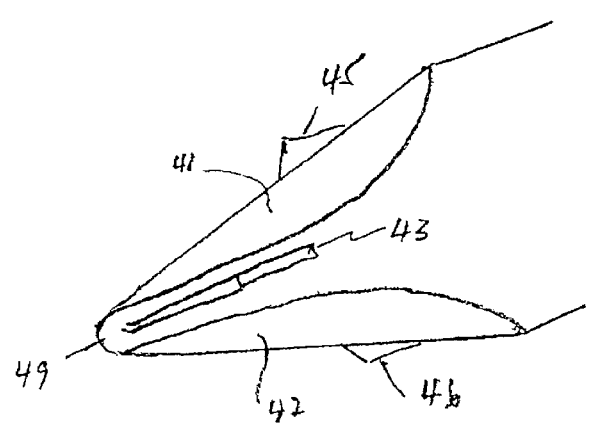
FIG. 3 is a perspective side view of a tip for an obturator in accordance with the present invention.

With reference to FIGS. 2 and 3, the distal end of obturator assembly 40 is shown in more detail. The distal end of the obturator comprises a tip which is non-conical and which has an upper face 41 and a lower face 42. Faces 41 and 42 taper from the shaft of the obturator assembly to form a V-shaped distal end 49. The tip has wing elements 43 and 44 provided on opposite sides of the distal end of the tip between the upper and lower faces 41 and 42, proximate the distal and of the tip. Wing elements 43 and 44 are spaced apart approximately 180 degrees. Each wing element 43, 44 has a distal edge which may be blunt to assist in tissue separation or may be sharp to assist in a cutting operation. The wing elements may be formed from metal or a hard plastic material.

With reference still to FIGS. 2 and 3, the distal end of the obturator shaft may also include dorsal elements 45 and 46 which are provided on the upper and lower faces 41 and 42, respectively. The dorsal elements may also be formed from metal or a hard plastic material.

With a trocar in accordance with the present invention, it is believed that less force will be required to insert the obturator into a patient than the force required with conventional trocars. Additionally, the design of the tip of the trocar as illustrated in FIGS. 2 and 3, forces the penetration pressure to points away from the tip, which eases the penetration of the trocar into the patient.

In accordance with the present invention, the distal tip of the obturator is made of plastic and is preferably replaceable. This replaceability allows the surgeon to use a tip which has wing elements that are sharp for cutting tissue or blunt for the separation of tissue. The techniques for making replaceable tips for trocars is well-known in the art, for example as shown in U.S. Pat. No. 5,697,947 to Wolf, which is incorporated herein by reference.

The foregoing and other advantages of the invention will be apparent to those skilled in the art.

What is claimed is:

1. A trocar, comprising:
   a. a body assembly;
   b. a cannula assembly attached to the body assembly to define a bore therethrough; and
   c. an obturator assembly for sliding engagement in the bore, which obturator assembly comprises: (i) a shaft having a distal end for insertion into a patient, where the distal end of the obturator has a tip which is non-conical and which has an upper face and a lower face which taper from the shaft to form a V-shaped distal end of the tip; and (ii) blunt wing elements which are located between the upper and lower faces proximate the distal end of the obturator which are spaced approximately 180 degrees from one another.

2. A trocar, comprising:
   a. a body assembly;
   b. a cannula assembly attached to the body assembly to define a bore therethrough;
   c. an obturator assembly for sliding engagement in the bore, which obturator assembly comprises: (i) a shaft having a distal end for insertion into a patient, where the distal end of the obturartor has a tip which is non-conical and which has an upper face and a lower face which taper from the shaft to form a V-shaped distal end of the tip; and (ii) wing elements which are located between the upper and lower faces proximate the distal end of the obturator which are spaced approximately 180 degrees from one another; and
   d. a dorsal element on the upper and lower faces of the obturator tip.

* * * * *